United States Patent [19]

Ueno

[11] Patent Number: 4,870,973
[45] Date of Patent: Oct. 3, 1989

[54] ELECTRONIC BLOOD PRESSURE METER HAVING MEANS FOR DETECTING ARTIFACTS

[75] Inventor: Satoshi Ueno, Kyoto, Japan

[73] Assignees: Omron Tateisi Electronics Co.; Isao KAI, both of Kyoto, Japan

[21] Appl. No.: 192,574

[22] Filed: May 11, 1988

[30] Foreign Application Priority Data

May 13, 1987 [JP] Japan ................................. 62-116435

[51] Int. Cl.$^4$ ............................................... A61B 5/02
[52] U.S. Cl. ..................................... 128/680; 128/687
[58] Field of Search .......................... 128/672, 677-686, 128/687-690

[56] References Cited

U.S. PATENT DOCUMENTS

| | | | |
|---|---|---|---|
| 3,791,378 | 2/1974 | Hochberg et al. ................... | 128/682 |
| 4,223,681 | 9/1980 | Sherman ............................ | 128/672 |
| 4,408,614 | 10/1983 | Weaver et al. ...................... | 128/680 |
| 4,677,983 | 7/1987 | Yamaguchi et al. ................ | 128/680 |
| 4,777,959 | 10/1988 | Wallach et al. ................... | 128/672 X |

*Primary Examiner*—Angela D. Sykes
*Attorney, Agent, or Firm*—Wegner & Bretschneider

[57] ABSTRACT

In an electronic blood pressure meter, artifacts or disturbances of blood pressure measurement due to the motions of the arm or the body of the person whose blood pressure is to be measured is detected from the level of a pulse wave signal. If the pulse wave signal continues to be above a certain reference level for more than a certain threshold time period, it is determined to be indicative of the presence of an artifact which prevents accurate measurement of blood pressure. This process of detecting an artifact can be conveniently implemented as an interruption routine of a microprocessor. When such an artifact is detected, a warning signal may be issued and the cuff may be rapidly vented so that the renewed measurement can be carried out without any further ado.

3 Claims, 4 Drawing Sheets

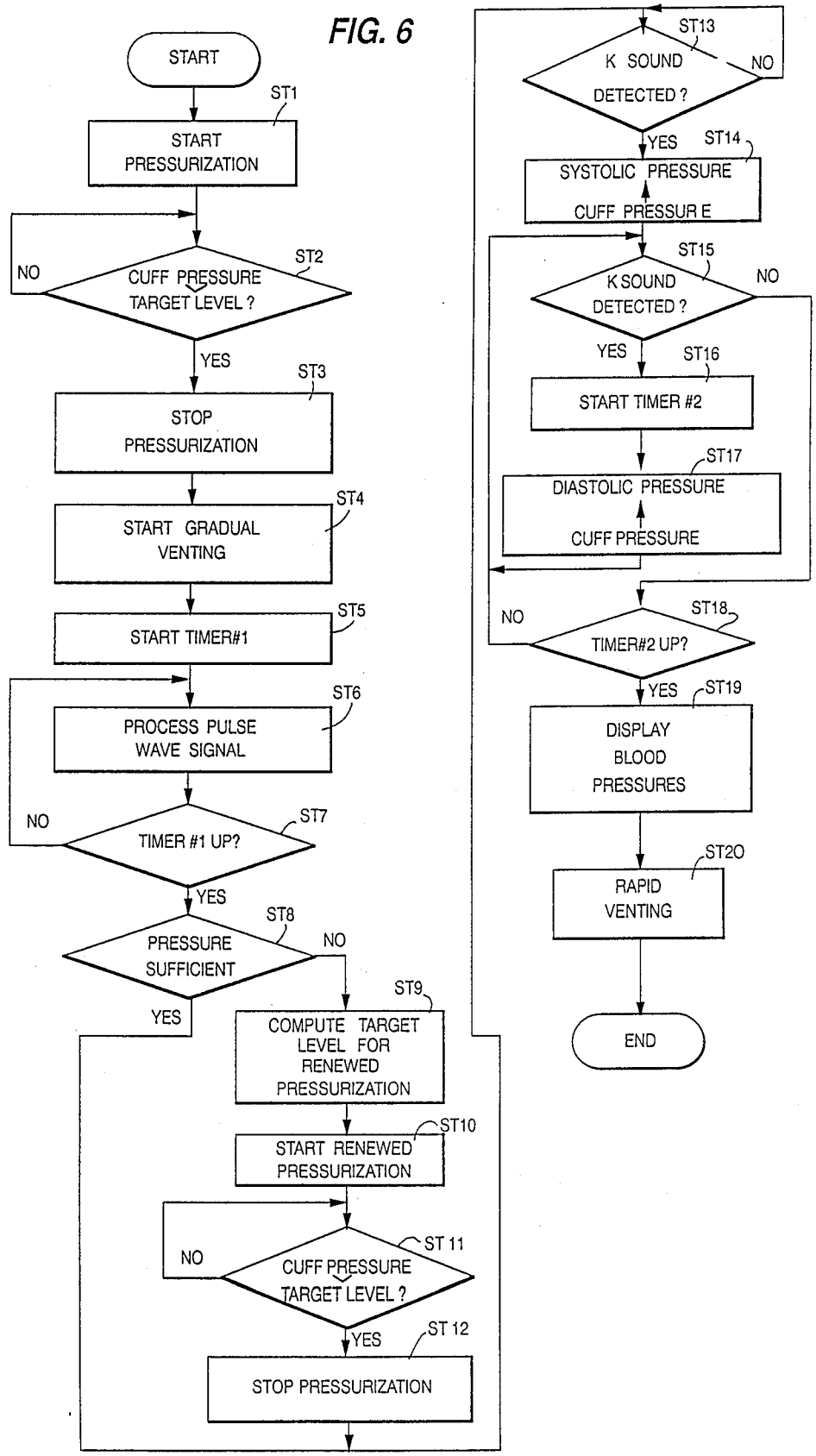

ELECTRONIC BLOOD PRESSURE METER HAVING MEANS FOR DETECTING ARTIFACTS

TECHNICAL FIELD

The present invention relates to an electronic blood pressure meter and in particular to such an electronic blood pressure meter which can detect artifacts (motion of the arm or of the body) which may affect the accuracy of the measurement of blood pressure so that generation of inaccurate measurement results may be prevented.

BACKGROUND OF THE INVENTION

In a typical conventional electronic blood pressure meter (for instance, of an oscillation type), after a cuff is wrapped around an arm of a person and is initially pressurized to a certain level, the cuff is gradually depressurized. During this depressurization process, a DC component of the cuff pressure signal is detected and a pulse wave component contained in the cuff pressure signal is extracted at the same time. A maximum amplitude of this pulse wave signal is obtained, for instance for each pulse and an envelope of the maximum amplitudes arranged in time series (cuff pressure series) is obtained. Two levels of blood pressure are determined from this envelope and the DC component of the cuff pressure according to a certain algorithm. A typical algorithm for determining blood pressure values consists of determining an average blood pressure from the cuff pressure corresponding to the maximum value of the parameter (envelope), a systolic blood pressure from the cuff pressure of a high pressure side when the parameter corresponds to 50% of the maximum value, and a diastolic blood pressure from the cuff pressure of a low pressure side when the parameter corresponds to 70% of the maximum value.

In such an oscillation type electronic blood pressure meter, the pressure sensor can obtain an accurate distribution of the parameter only when it is attached to a proper position in an upper arm of the person and kept in the same position throughout the measurement. Therefore, when artifacts such as the motions of the arm or the body should arise during measurement, the distribution of the parameter as detected becomes distorted (See FIG. 5) and accurate determination of blood pressures according to the normal algorithm becomes impossible. This is highly inconvenient because a great care is required for blood pressure measurement and, yet, inaccurate measurements could still occur without being noticed.

Japanese Patent Laid Open Publication No. 61-196936 filed by the assignee of the present application discloses an electronic blood pressure meter which detects artifacts during measurement and permits accurate measurement of blood pressures. This electronic blood pressure meter comprises first determination means for comparing a current parameter value obtained by a pulse wave parameter extraction means with a previous parameter value and determining whether the current parameter value is greater than the previous parameter value or not, first difference computing means for computing a first difference value between the current parameter value and the previous parameter value, second determination means for determining whether the first difference value is greater than a predetermined value or not, second difference computing means for computing a second difference value between the previous parameter value and the yet previous parameter value, and third determination means for determining whether the second difference value is substantially greater than the first difference value or not, and the parameter value is determined to be abnormal when all the outputs from the first, the second and the third determination means are affirmative.

According to this previously proposed electronic blood pressure meter, the current parameter value is estimated to be abnormal when the first difference value obtained by the first computing means is determined to be greater than the predetermined value by the second determination means. Further, if the second difference value computed by the second computing means is determined to be substantially greater than the first difference value by the third determination means, it means that the parameter value has just sharply increased and it is estimated that an artifact may have affected the current parameter value. It also means that the measurement was not accurate and is required to be started all over again.

However, this method is based on the comparison of a plurality of pulse wave amplitudes or pulse wave parameter values and, therefore, a sufficient number of amplitude values must be made available before abnormal conditions (artifacts) can be detected. Therefore, a considerable time must be spent before being able to determine whether the measurement has been carried out in proper manner or not. Furthermore, the algorithm for these comparison processes is so complex that the response time of the machine or the microprocessor tends to be long and the cost of the electronic blood pressure meter increases due to added complexity of the hardware. Furthermore, criteria of the comparison processes may not be appropriate for all the persons whose blood pressures are to be measured and it was indeed found by the inventor that accurate detection of artifacts is sometimes not possible for certain individuals.

BRIEF SUMMARY OF THE INVENTION

In view of such problems of the prior art, a primary object of the present invention is to provide an improved electronic blood pressure meter which can readily and quickly determine the presence of artifacts.

A second object of the present invention is to provide an electronic blood pressure meter which can detect artifacts and is yet simple in structure and economical to manufacture.

These and other objects of the present invention can be accomplished by providing: an electronic blood pressure meter, comprising: a cuff; pressurization means for pressurizing the cuff; depressurization means for depressurizing the cuff; pressure detecting means for detecting the pressure in the cuff; blood vessel information detecting means for detecting blood vessel information during the process of pressurization or depressurization of the cuff; and blood pressure values determining means for determining a systolic blood pressure and a diastolic blood pressure according to output signals from the blood vessel information detecting means and the pressure detecting means; further comprising: pulse wave component detecting means for obtaining pulse wave data; non-negative time period measuring means for measuring a non-negative time period of the pulse wave data obtained by the pulse wave component detecting means; and abnormal state detecting means for detecting an abnormal state when the non-negative time period measured by the non-negative time period measuring means is greater than a certain threshold level.

According to an electronic blood pressure meter having these structural characteristics, pulse wave data is detected, for instance once every 10 msec with the pulse wave detecting means and a non-negative period of the pulse wave data for each pulse is measured. Then, it is determined whether the nonnegative period of the pulse wave data is greater than the predetermined value (for instance, 1.5 seconds) or not, and if so, it is then estimated that an artifact is present. Each pulse wave data is detected every time the pulse wave data crosses a certain reference level and the positive period (non-negative period) during which the pulse wave data is above the reference level is thus dependent on the number of pulses for a given time. The pulse count varies from one individual to another, but is generally between 60 and 80 pulses per minute Accordingly, the predetermined value (predetermined time period which is to be compared with the non-negative time period) is selected to be 1.5 seconds (which corresponds to 40 pulses per minute). Therefore, when the non-negative time period is greater than 1.5 seconds, it is highly likely that an artifact is present and the measurement of blood pressures will be inaccurate.

According to a preferred embodiment of the present invention, the abnormal state detecting means consists of an action of a programmed microprocessor which is repeatedly carried out at a certain time interval by interrupting a main routine for normal measurement of blood pressure values When the abnormal state detecting means has detected an abnormal state, a warning signal may be issued and the cuff may be rapidly vented so that the renewed measurement of blood pressure may be quickly started all over again. And, the threshold level may correspond to a time interval which is approximately 1.5 seconds or longer This threshold level corresponds to the pulse rate of 40 pulses per minute and is quite unlikely to be a pulse interval of a normal person.

BRIEF DESCRIPTION OF THE DRAWINGS

Now the present invention is described in the following in terms of a specific embodiment with reference to the appended drawings, in which:

FIG. 6 is a flow chart showing the action of the electronic blood pressure meter according to the present invention.

DETAILED DESCRIPTION OF THE PREFERRED EMBODIMENT

Figure 4:
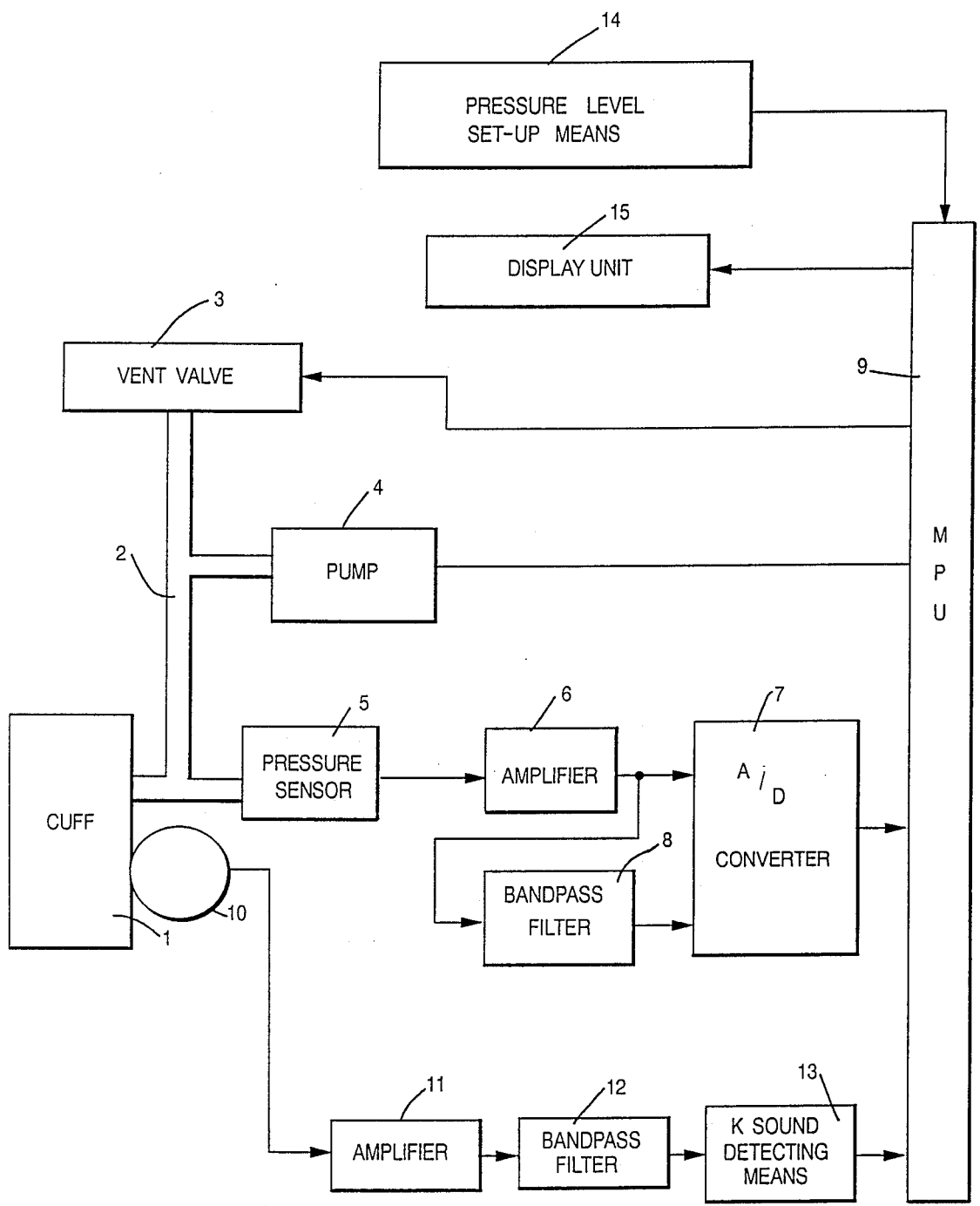
FIG. 4 is an overall functional block diagram of the electronic blood pressure meter according to the present invention.

FIG. 4 shows a block diagram of the air flow system and the electronic system of an embodiment of the electronic blood pressure meter according to the present invention. There is shown a cuff 1 connected to a pressurization pump (pressurization means) 4, a vent valve (venting means) 3 and a pressure sensor (pressure detecting means) 5 by way of a conduit 2.

The vent valve 3 actually consists of a rapid vent valve and a slow vent valve. The pressure sensor 5 may consist of a diaphragm pressure transducer using a strain gauge. The pressurization pump 4 and the vent valve 3 are controlled by an MPU (microprocessor unit) 9 as described hereinafter.

The analog output signal from the pressure sensor 5 is amplified by an amplifier 6 and is converted into a digital signal by an AD converter 7. The MPU 9 reads the digitalized output signal from the pressure sensor 5 at an equal interval. The output signal from the pressure sensor 5 which is amplified by the amplifier 6 is also supplied to a bandpass filter 8 which extracts a pulse wave component contained in the cuff pressure signal to supply it to the MPU 9.

The cuff 1 is further provided with a K sound sensor (microphone) 10 which outputs a K (Korotkoff) sound signal. The K sound signal is amplified by an amplifier 11 and after its noise components are removed by a bandpass filter 12 is then supplied to the MPU 9 by way of a K sound detector 13.

The MPU 9 has the functions of determining a systolic blood pressure and a diastolic blood pressure from the K sound signal and the cuff pressure signal. The MPU 9 controls a pressure level set-up device 14 which determines the target value to which the cuff 1 is to be pressurized and a display unit 15 for displaying a systolic blood pressure and a diastolic blood pressure.

Figure 3:
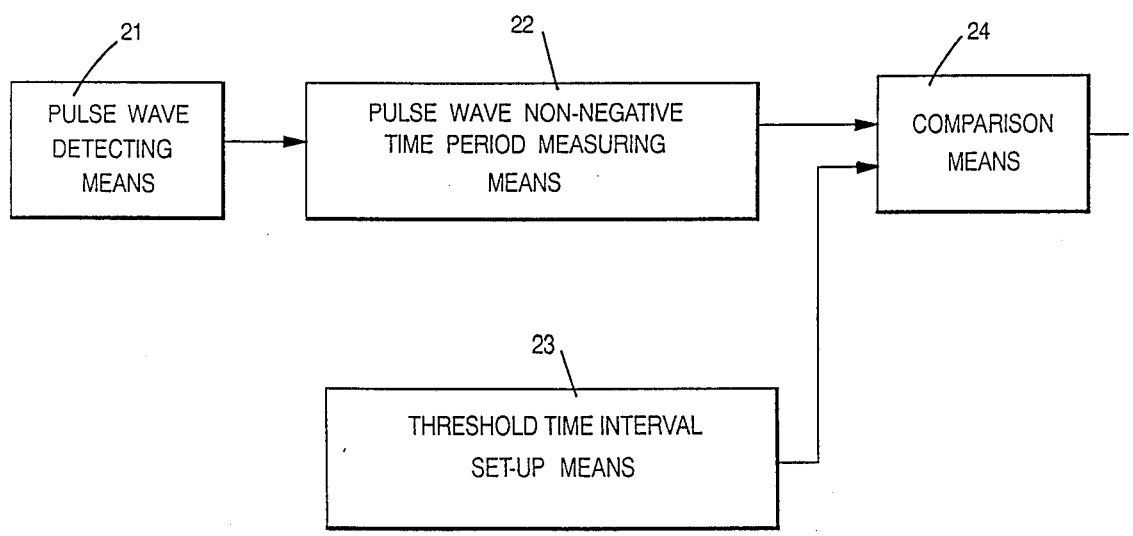
FIG. 3 is a functional block diagram of an essential part of an electronic blood pressure meter according to the present invention.

As shown in the block diagram of FIG. 3, the MPU 9 is further provided with the function (pulse wave non-negative time period measuring means 22) of measuring the non-negative time period of the pulse wave data obtained by a pulse wave detector 21 (the bandpass filter 8), the function (time set-up means 23) of setting up a predetermined time period (1.5 seconds in the present embodiment) which is to be compared with the non-negative time period detected by the pulse wave non-negative time period measuring means 22, and the function (abnormal state detecting means or comparing means 24) of comparing the measured time period with the predetermined time period. Presence of an artifact is determined when the non-negative time period is greater than 1.5 seconds. This time period of 1.5 seconds corresponds to the pulse rate of 40 pulses per minute and is selected to be highly unlikely for a normal person. In other words, the fact that the positive time period of each pulse data is greater than 1.5 seconds means a pulse rate of less than 40 pulses per second. Since this can not possibly be a correct value, the presence of an artifact is estimated with a very high likelihood.

FIG. 6 is a flow chart of the control action of the electronic blood pressure meter of the present embodiment.

When the system is started by pressing a start key not shown in the drawings, the pressurization pump 4 is activated by a control signal from the MPU 9 and the cuff 1 is pressurized (ST 1) until the pressure level reaches a predetermined pressure level which was initially set up by the pressure level set-up means 14. When the cuff pressure has reached this level, the determination result of ST 2 becomes affirmative and the pressurization of the cuff 1 is terminated by stopping the pressurization pump 4 (ST 3). Then, a gradual depressurization of the cuff 1 is started by a control signal from the MPU 9 (ST 4) and a three-second timer (timer #1) is started (ST 5). The subsequently obtained pulse wave data is digitalized by the AD converter 7 and is stored in a memory area for executing the processing of the pulse wave signal (ST 6). This processing of the pulse wave signal in ST 6 is continued for three seconds (ST 7).

Thereafter, sufficiency of the cuff pressure is determined (ST 8), or, in other words, it is determine whether the cuff pressure is sufficient for obtaining a systolic blood pressure or not. If the cuff pressure is found to be insufficient, the system flow advances from the determination step of ST 8 to the step of computing a target value for renewed pressurization (ST 9) and the renewed pressurization is started (ST 10). When the cuff 1 has been pressurized to the target value by the renewed pressurization, since the cuff pressure has become higher than the target value by the renewed pressurization, the system flow advances from the determination step of ST 11 to the step of terminating the depressurization of the cuff 1 in ST 12. Thereafter, the gradual venting is performed and the steps of measuring blood pressures are executed as described hereinafter in the same way as the case in which the determination result of ST 8 is positive.

In the present embodiment, the measurement of the blood pressures is based on the detection of the Korotkoff sound (K sound). It is determined in ST 13 whether the K sound has been detected or not. If the K sound has been detected, the system flow advances from ST 13 to ST 14 where the current cuff pressure is determined as a systolic blood pressure. Thereafter, detection of the K sound is continued until the K sound has totally disappeared and as long as the K sound is being detected, the determination result of ST 15 (whether the K sound is being detected or not) is affirmative and a three-second timer (timer #2) is started (ST 16). Subsequently, the current cuff pressure upon detection of the K sound is temporarily assumed as a diastolic pressure and its value is stored in memory (ST 17). This process is continued every three seconds until the K sound has totally disappeared.

Now, if the K sound has disappeared, the determination result of ST 15 becomes negative and it is then determined whether the timer #2 has timed up or not (ST 18). If the three second timer #2 has timed up, the determination result of ST 18 becomes affirmative and the cuff pressure at the time when the K sound has disappeared is determined as a final diastolic pressure. Then, the systolic blood pressure and the diastolic blood pressure are both displayed on the display unit 15 (ST 19) and the vent valve 3 is opened up to rapidly vent the cuff 1 (ST 20). This completes the measurement of the blood pressures.

Figure 2:
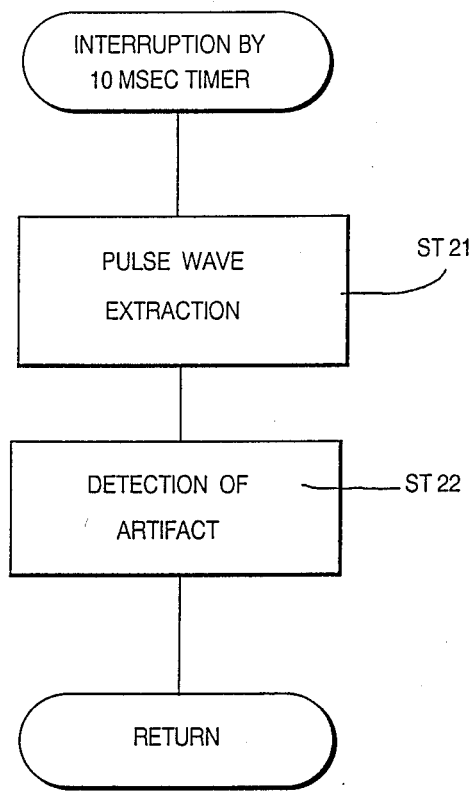
FIG. 2 is a flow chart of an interruption process for detecting artifacts according to the present invention.

While this main routine is being executed, the following interruption routine shown in FIG. 2 may be executed as required.

Figure 1:
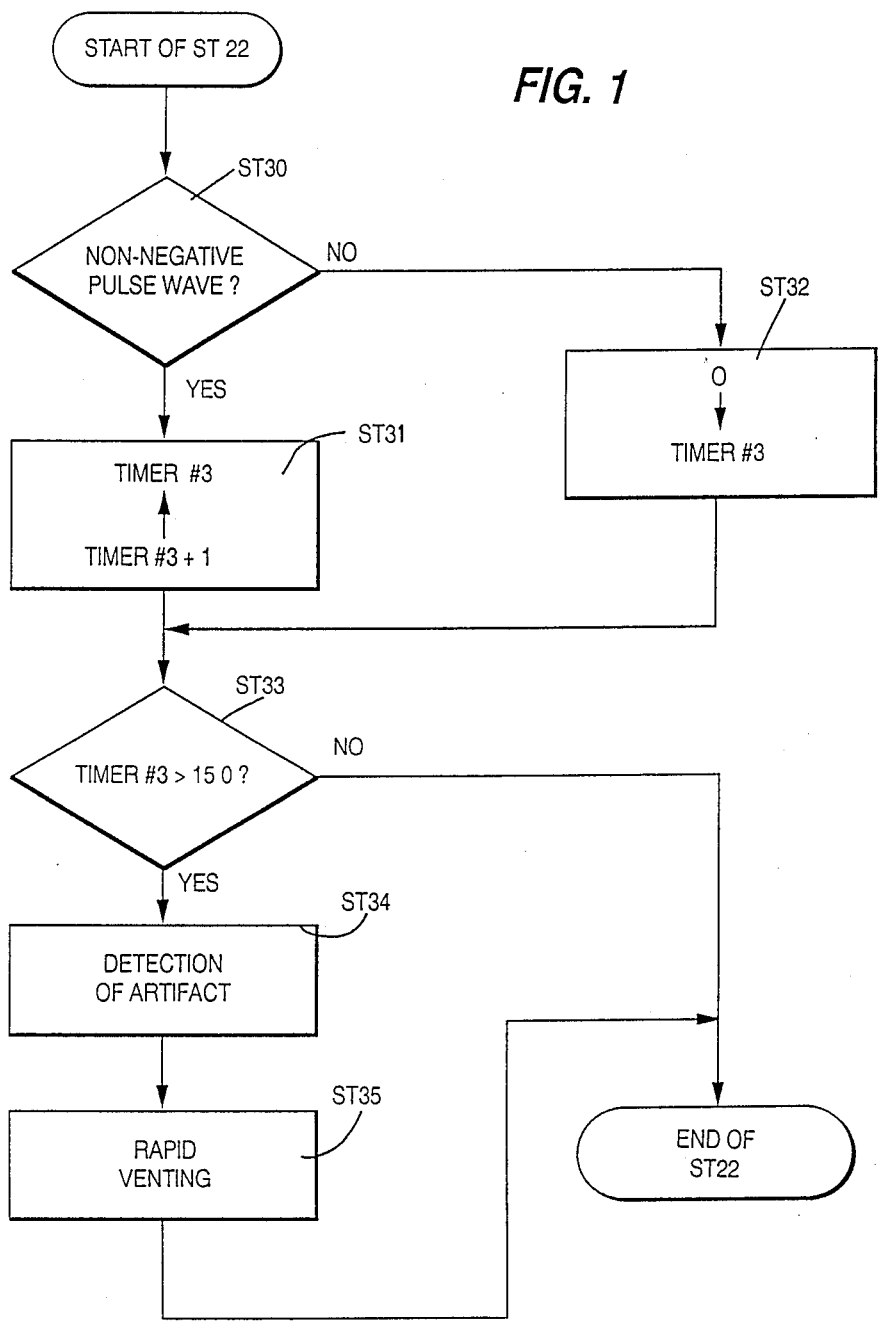
FIG. 1 is a flow chart of the process of detecting artifacts or disturbances due to the motion of the body according to the present invention.
Figure 5:
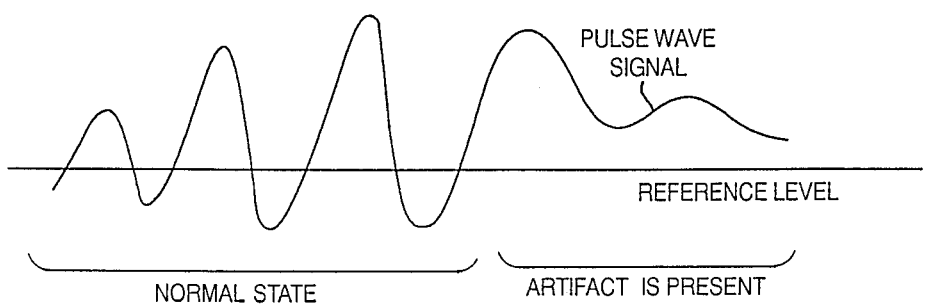
FIG. 5 is a graph showing how a pulse wave signal could be affected by an artifact.

In the present embodiment, the MPU 9 is so programmed that the interruption routine is executed every 10 msec. In other words, in every 10 msec, the extraction of the pulse wave and the AD conversion of the pulse wave are executed (ST 21) and the process of detecting artifacts is performed (ST 22) as described hereinafter. After the artifacts are detected, the system flow returns to the point where the last interruption routine was called, and the routine of measuring the blood pressures is resumed. FIG. 1 shows an essential part of the process of detecting the artifacts such as the motion of the body or the arm.

The pulse wave signal (pulse wave data) which is extracted every 10 msec is determined to be positive or not (non-negative or not) in ST 30. In other words, every time the pulse wave data of each pulse crosses over a threshold level, it is determined whether this cross over point is that of an increasing pulse wave data or not (ST 30). If it is found that the pulse wave data is positive (or has risen over the reference level and is therefore positive), the timer #3 is started. Otherwise or if the pulse wave signal is negative (or has dropped below the reference level and is therefore negative), the determination result is negative and the timer #3 is reset to a zero state (ST 32). Therefore, in this case, the determination result of ST 33 (where it is determined whether the reading of the timer #3 is greater than 150 or not as described hereinafter) is also negative and the detection of artifacts is completed.

On the other hand, if the pulse wave signal is positive, the determination result of ST 30 is affirmative and "1" is added to the reading of the timer #3 in ST 31. This timer #3 measures the time interval during which the pulse wave signal is non-negative by the unit of msec and it was set to "0" in ST 3 of terminating the pressurization in the main routine (FIG. 6).

In ST 33, it is determined whether the timer reading is greater than 150 or not. In other words, since the unit of the reading of the timer #3 is 10 msec, the predetermined value of 150 corresponds to 1,500 msec or 1.5 seconds. Therefore, the determination step of ST 33 determines whether the timer reading has reached 1.5 seconds or not, and if the positive state of the pulse wave signal has changed into the negative state within 1.5 seconds, the determination result of ST, 33 becomes negative and the process of detecting artifacts is completed. However, if the positive state of the pulse wave signal has persisted for more than 1.5 seconds, the determination result of ST 33 becomes affirmative and detection of an artifact is notified by sounding of a buzzer in ST 34. Then, the cuff 1 is rapidly vented and the process of detecting an artifact is completed (ST 36) so that the measurement may be performed all over again.

Thus, according to the present invention, in an electronic blood pressure meter, artifacts or disturbances of blood pressure measurement due to the motions of the arm or the body of the person whose blood pressure is to be measured is detected from the level of a pulse wave signal. If the pulse wave signal continues to be above a certain reference level for more than a certain threshold time period, it is determined to be indicative of the presence of an artifact which prevents accurate measurement of blood pressure. This process of detecting an artifact can be conveniently implemented as an interruption routine of a microprocessor. When such an artifact is detected, a warning signal may be issued and the cuff may be rapidly vented so that the renewed measurement can be carried out without any further ado.

The electronic blood pressure meter described above was based on the detection of the K sound for determining the blood pressure values, but the present invention is equally applicable to oscillation type electronic blood pressure meters.

Although the present invention has been shown and described with reference to the preferred embodiment thereof, it should not be considered as limited thereby.

Various possible modifications and alterations could be conceived of by one skilled in the art to any particular detail of the embodiment, without departing from the scope of the invention.

What we claim is:

1. An electronic blood pressure meter, comprising:
   a cuff;
   pressurization means for pressurizing the cuff;
   depressurization means for depressurizing the cuff;
   pressure detecting means for detecting the pressure in the cuff;
   blood vessel information detecting means for detecting blood vessel information during the process of pressurization or depressurization of the cuff; and
   blood pressure values determining means for determining a systolic blood pressure and a diastolic blood pressure according to output signals from the blood vessel information detecting means and the pressure detecting means;
   further comprising:
   pulse wave component detecting means connected to the cuff, the pulse wave component detecting means being for obtaining pulse wave data;
   non-negative time period measuring means for measuring a non-negative time period of the pulse wave data obtained by the pulse wave component detecting means, the non-negative time period being measured relative to a certain reference level;
   abnormal state detecting means for detecting an abnormal state when the non-negative time period measured by the non-negative time period measuring means is greater than a certain threshold level; and
   wherein the abnormal state detecting means comprises a microprocessor which is repeatedly activated at a certain time interval by interrupting a main routine for normal measurement of blood pressure values.

2. An electronic blood pressure meter as defined in claim 1, wherein a warning signal is issued and the cuff is rapidly vented when the abnormal state detecting means has detected an abnormal state.

3. An electronic blood pressure meter as defined in claim 1, wherein the threshold level corresponds to a time interval which is approximately 1.5 seconds or longer.

* * * * *